United States Patent [19]

Stern et al.

[11] Patent Number: 5,331,099
[45] Date of Patent: Jul. 19, 1994

[54] PROCESS FOR PREPARING P-NITROAROMATIC AMIDES AND PRODUCTS THEREOF

[75] Inventors: Michael K. Stern; James K. Bashkin, both of University City, Mo.

[73] Assignee: Monsanto Company, St. Louis, Mo.

[21] Appl. No.: 45,309

[22] Filed: Apr. 16, 1993

Related U.S. Application Data

[63] Continuation-in-part of Ser. No. 888,999, May 22, 1992, abandoned.

[51] Int. Cl.$^5$ .......................................... C07C 231/08
[52] U.S. Cl. .................... 564/154; 564/156; 564/157; 564/158; 564/162; 564/164; 564/166; 564/179; 564/184; 564/219; 564/220; 564/414; 564/441
[58] Field of Search ............... 564/154, 156, 157, 158, 564/166, 184, 164, 179

[56] References Cited

U.S. PATENT DOCUMENTS

| | | | |
|---|---|---|---|
| 3,414,616 | 12/1968 | Summers et al. | 260/566 |
| 3,847,990 | 11/1974 | Blahak | 260/576 |
| 4,122,118 | 10/1978 | George et al. | 260/576 |
| 4,140,716 | 2/1979 | Maender et al. | 260/562 R |
| 4,155,936 | 5/1979 | Sturm | 260/576 |
| 4,178,315 | 12/1979 | Zengel et al. | 260/647 |

(List continued on next page.)

FOREIGN PATENT DOCUMENTS

| | | |
|---|---|---|
| 293999 | 12/1988 | European Pat. Off. . |
| 453885 | 10/1991 | European Pat. Off. . |
| 1440767 | 6/1976 | United Kingdom . |

OTHER PUBLICATIONS

Ayyangar, N. R. et al., "A Novel Reaction of Acetanilide with Nitrobenzene in DMSO—An Unusual Solvent Assisted Regioselective Aromatic Nucleophilic Substitution", *Tetrahedron Letters,* vol. 31, No. 22, pp. 3217–3220 (1990).

(List continued on next page.)

*Primary Examiner*—Allen J. Robinson
*Assistant Examiner*—Brian M. Burn
*Attorney, Agent, or Firm*—Kenneth D. Goetz; Paul L. Passley; James C. Bolding

[57] ABSTRACT

A process for preparing p-nitroaromatic amides is provided which comprises contacting an amide and nitrobenzene in the presence of a suitable solvent system, and reacting the amide and nitrobenzene in the presence of a suitable base and a controlled amount of protic material at a suitable temperature in a confined reaction zone. The p-nitroaromatic amides of the invention can be reduced to p-aminoaromatic amides. In one embodiment, the p-aminoaromatic amide is further reacted with ammonia under conditions which produce the corresponding p-aminoaromatic amine and the amide starting material which can be recycled or with water in the presence of a suitable basic or acidic catalyst under conditions which produce the corresponding p-aminoaromatic amine and the acid or salt thereof corresponding to the amide starting material. In another embodiment, the p-aminoaromatic amine is reductively alkylated to produce alkylated p-aminoaromatic amine. The p-nitroaromatic amide can be reacted with ammonia under conditions which produce the corresponding p-nitroaromatic amine and the amide starting material which can be recycled or with water in the presence of a suitable basic or acidic catalyst under conditions which produce the corresponding p-nitroaromatic amine and the acid or salt thereof corresponding to the amide starting material. In one embodiment, the p-nitroaromatic amine is reduced to produce p-aminoaromatic amine. In another embodiment, the p-aminoaromatic amine is reductively alkylated to produce alkylated p-aminoaromatic amine. In another embodiment, the p-nitroaromatic amine is reductively alkylated to produce p-aminoaromatic amine.

77 Claims, No Drawings

U.S. PATENT DOCUMENTS

| | | | |
|---|---|---|---|
| 4,187,248 | 2/1980 | Merten et al. | 260/576 |
| 4,187,249 | 2/1980 | Maender et al. | 260/576 |
| 4,196,146 | 4/1980 | Merten et al. | 260/576 |
| 4,209,463 | 6/1980 | Maender et al. | 260/576 |
| 4,404,401 | 9/1983 | Zengel et al. | 564/416 |
| 4,463,191 | 7/1984 | D'Sidocky et al. | 564/398 |
| 4,479,008 | 10/1984 | Batorewicz et al. | 564/433 |
| 4,518,803 | 5/1985 | Batorewicz et al. | 564/410 |
| 4,614,817 | 9/1986 | Maender et al. | 564/406 |
| 4,670,595 | 6/1987 | Podder et al. | 564/406 |
| 4,683,332 | 7/1987 | Sturm | 564/414 |
| 4,760,186 | 7/1988 | Solodar | 564/415 |
| 4,900,868 | 2/1990 | Merten et al. | 564/398 |

OTHER PUBLICATIONS

Wohl, A., "Toward the Knowledge of the Reaction Between Nitrobenzene and Aniline in the Presence of Alkali", *Chemische Berichte*, 36, pp. 4135–4138 (1903).

Wohl, A. and Aue, W., *Chemische Berichte*, 34, pp. 2442–2450 (1901).

Banerjee, A. A. and Mukesh, D., "Heterogeneous Catalytic Transfer Hydrogenation of 4–Nitrodiphenylamine to p–Phenylenediamines", *J. Chem. Soc., Chem. Comm.*, 18, 1275–76 (1988).

Rylander, W. P., "Catalytic Hydrogenation in Organic Synthesis", Academic Press, p. 299 (1979).

Jencks, W. P., *J. Am. Chem. Soc.*, 92, 3201–3202 (1970).

PROCESS FOR PREPARING P-NITROAROMATIC AMIDES AND PRODUCTS THEREOF

CROSS REFERENCE TO RELATED APPLICATION

This application is a continuation-in-part of application Ser. No. 07/888,999, filed May 22, 1992, now abandoned.

BACKGROUND OF THE INVENTION

This invention relates to the production of p-nitroaromatic amides. In one aspect, this invention relates to the production of p-aminoaromatic amides. In another aspect, this invention relates to the production of p-nitroaromatic amines. In a further aspect, this invention relates to the production of p-aminoaromatic amines. In a still further aspect, this invention relates to the production of alkylated p-aminoaromatic amines.

Aromatic amide bonds are currently formed by the reaction of an amine with an acid chloride. Specifically, it is known to prepare p-nitroaromatic amides by the reaction of a nitroaromatic amine with an acid chloride. This process is disadvantageous in that the halide that is displaced is corrosive to the reactors and appears in the waste stream and must therefore be disposed of at considerable expense. Furthermore, the nitroaromatic amine is prepared by the reaction of halonitroaromatic, e.g., chloronitrobenzene, and ammonia and results in the same displacement of halide causing additional corrosion and waste disposal problems. Therefore, a non-halide route to substituted aromatic amides and specifically nitroaromatic amides and products thereof would provide significant advantages over current technology and result in a more efficient and economic commercial process.

The process of the invention is such a non-halide route to nitroaromatic amides and products thereof and therefore eliminates the expensive halide removal from the waste stream as well as corrosion problems caused by the halide.

SUMMARY OF THE INVENTION

It is an object of the invention to provide a process for producing p-nitroaromatic amides for use in the preparation of p-nitroaromatic amines, p-aminoaromatic amines, p-aminoaromatic amides and alkylated p-aminoaromatic amines. It is a further object of the invention to provide an efficient and economic process to produce p-nitroaromatic amides and products thereof that is commercially viable. It is a further object of the invention to provide a process for producing p-aminoaromatic amines for use as monomers in the production of polyamides or other polymer applications. It is a still further object of the invention to provide a process for producing alkylated p-aminoaromatic amines for use as antioxidants or antiozonants. It is a still further object of the invention to provide a process for producing p-nitroaromatic amines for use as intermediates to anti-oxidants.

According to the invention, a process for preparing p-nitroaromatic amides is provided which comprises contacting an amide and nitrobenzene in the presence of a suitable solvent system, and reacting the amide and nitrobenzene in the presence of a suitable base and a controlled amount of protic material at a suitable temperature in a confined reaction zone. In one embodiment of the invention, the amount of protic material present during the reaction of amide and nitrobenzene is controlled by having a desiccant present during the reaction. In another embodiment, the amount of protic material present during the reaction of amide and nitrobenzene is controlled by continuously removing protic material by distillation.

Further according to the invention, a process for preparing p-aminoaromatic amides is provided which comprises reducing the p-nitroaromatic amides prepared according to the invention. In one embodiment, the p-aminoaromatic amide is further reacted with ammonia under conditions which produce the corresponding p-aminoaromatic amine and the amide starting material which can be recycled. In another embodiment, the p-aminoaromatic amide is further reacted with water in the presence of a suitable basic or acidic catalyst under conditions which produce the corresponding p-aminoaromatic amine and the acid or salt thereof corresponding to the amide starting material. In a further embodiment, the p-aminoaromatic amine is reductively alkylated to produce alkylated p-aminoaromatic amine.

Further according to the invention, the process for preparing p-nitroaromatic amines is provided which comprises reacting the p-nitroaromatic amide prepared according to the invention with ammonia under conditions which produce the corresponding p-nitroaromatic amine and the amide starting material which can be recycled or with water in the presence of a suitable basic or acidic catalyst under conditions which produce the corresponding p-nitroaromatic amine and the acid or salt thereof corresponding to the amide starting material. In one embodiment, the p-nitroaromatic amine is reduced to produce p-aminoaromatic amine. In another embodiment, the p-nitroaromatic amine is reductively alkylated to produce alkylated p-aminoaromatic amine. In another embodiment, the p-aminoaromatic amine is reductively alkylated to produce alkylated p-amino aromatic amine.

DETAILED DESCRIPTION OF THE INVENTION

The invention relates to a process for preparing p-nitroaromatic amides comprising:

(a) contacting an amide and nitrobenzene in the presence of a suitable solvent system, and (b) reacting the amide and nitrobenzene in the presence of a suitable base and a controlled amount of protic material at a suitable temperature in a confined reaction zone.

For producing p-aminoaromatic amides, the process of the invention further comprises:

(c) reducing the reaction product of (b) under conditions which produce p-aminoaromatic amides.

For producing p-aminoaromatic amines from p-aminoaromatic amides, the process of the invention further comprises:

(d) reacting the p-aminoaromatic amide with ammonia under conditions which produce the corresponding p-aminoaromatic amine and amide.

Alternatively, for producing p-aminoaromatic amines from p-aminoaromatic amides, the process of the invention further comprises:

(d) reacting the p-aminoaromatic amide with water in the presence of a suitable basic or acidic catalyst under conditions which produce the corresponding p-aminoaromatic amine and the acid or salt thereof corresponding to the amide of (a).

For producing the alkylated p-aminoaromatic amine, the process of the invention further comprises:

(e) reductively alkylating the p-aminoaromatic amine.

For producing p-nitroaromatic amine, the process of the invention further comprises:

(c') reacting the reaction product of (b) with (i) ammonia or (ii) water in the presence of a suitable basic or acidic catalyst under conditions which produce the corresponding p-nitroaromatic amine and amide or the corresponding acid or salt thereof.

For producing alkylated p-aminoaromatic amine, the process of the invention further comprises:

(d') reductively alkylating the p-nitroaromatic amine.

For producing p-aminoaromatic amine, the process of the invention further comprises:

(d") reducing the p-nitroaromatic amine under conditions which produce the corresponding p-aminoaromatic amine.

For producing alkylated p-aminoaromatic amine, the process of the invention further comprises:

(e") reductively alkylating the p-aminoaromatic amine.

The p-nitroaromatic amide produced by the process of the invention can be in the form of the neutral compound, i.e., not in the form of a salt, and/or in the form of the salt of such p-nitroaromatic amide. The salt is produced in the reaction mixture from reaction of the p-nitroaromatic amide with the base. Thus, the reaction mixture produced in the process of the invention can include the p-nitroaromatic amide compound, or salts or mixtures thereof depending on the specific reaction conditions selected.

The molar ratio of amide to nitrobenzene can vary from about 1:1 to a large excess of nitrobenzene. When nitrobenzene is used as the suitable solvent for the reaction, nitrobenzene is preferably present in a large excess relative to the amide. When nitrobenzene is not used as the solvent for the reaction, the molar ratio of amide to nitrobenzene can vary over a wide range, but is preferably about 1:1.

Amides that can be employed according to the invention include aromatic amides, aliphatic amides, substituted aromatic amide derivatives, substituted aliphatic amide derivatives and diamides having the formula:

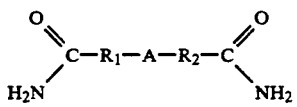

wherein $R_1$ and $R_2$ are independently selected from the group consisting of aromatic groups, aliphatic groups and a direct bond, and A is selected from the group consisting of

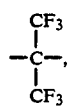

—SO$_2$—, —O—, —S— and a direct bond.

The aliphatic amides and substituted aliphatic amide derivatives that can be employed according to the invention are represented by the formula:

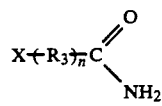

wherein n is 0 or 1, $R_3$ is selected from the group consisting of alkyl, arylalkyl, alkenyl, arylalkenyl, cycloalkyl and cycloalkenyl groups and X is selected from the group consisting of hydrogen, —NO$_2$, —NH$_2$, aryl groups, alkoxy groups, sulfonate groups, —SO$_3$H, —OH, —COH, —COOH, and alkyl, aryl, arylalkyl or alkyl aryl groups containing at least one —NH$_2$ group. Sulfonate groups, as used herein, are the esters of sulfonic acids. Examples of sulfonates include, but are not limited to, alkyl sulfonates, aralkyl sulfonates, aryl sulfonates and the like. The preferred alkyl and alkoxy groups contain from 1 to about 6 carbon atoms. The preferred aryl, arylalkyl and alkyl aryl groups contain from about 6 to about 18 carbon atoms.

Examples of aliphatic amides and substituted aliphatic amide derivatives include, but are not limited to, isobutyramide, urea, acetamide, propylamide and mixtures thereof.

As used herein, the term "substituted aromatic amide derivatives" means aromatic amides containing one or more electron withdrawing or electron releasing substituents on the aromatic ring. Applicable substituents include, but are not limited to, halides, —NO$_2$, —NH$_2$, alkyl groups, alkoxy groups, sulfonate groups, —SO$_3$H, —OH, —COH, —COOH, and alkyl, aryl, arylalkyl or alkyl- aryl groups containing at least one —NH$_2$ group. Halides are selected from the group consisting of chloride, bromide and fluoride. The preferred alkyl and alkoxy groups contain from 1 to about 6 carbon atoms. The preferred aryl, arylalkyl and alkyl aryl groups contain from about 6 to about 18 carbon atoms.

Examples of aromatic amides and substituted aromatic amide derivatives include, but are not limited to, benzamide, 4-methylbenzamide, 4-methoxybenzamide, 4-chlorobenzamide, 2-methylbenzamide, 4-nitrobenzamide, 4-aminobenzamide and mixtures thereof.

Diamides that can be employed according to the process of the invention include, but are not limited to, adipamide, oxalic amide, terephthalic diamide, 4,4'-biphenyldicarboxamide and mixtures thereof.

The reaction between the amide and nitrobenzene is carried out in a suitable solvent system. As used herein, the phase "suitable solvent system" means a polar aprotic solvent.

Suitable solvent systems include, but are not limited to, solvents such as, for example, nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxides or amides having a melting point below the reaction temperature, e.g., molten tetramethyl ammonium hydroxide and molten benzamide, and mixtures thereof. The currently preferred suitable solvents are nitrobenzene, dimethylsulfoxide, dimethylformamide and N-methyl-2-pyrrolidone. Most preferably, nitrobenzene is used in excess in the reaction as stated above, and the nitrobenzene in excess of the molar amount of amide serves as the solvent. As described in more detail below, solvent mixtures can be utilized wherein one or more of the suitable solvents and another solvent, such as a controlled amount of a protic solvent, are combined.

Examples of protic solvent include, but are not limited to, methanol, water and mixtures thereof.

Suitable bases include, but are not limited to, organic and inorganic bases such as alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetrasubstituted ammonium hydroxides or halides wherein each substituent is independently selected from alkyl, aryl or arylalkyl groups wherein the alkyl, aryl and arylalkyl groups preferably have 1 to about 18 carbon atoms, including tetraalkyl ammonium hydroxides, e.g., tetramethyl ammonium hydroxide, tetraalkyl ammonium halides, e.g., tetrabutyl ammonium chloride, aryl, trialkyl ammonium hydroxides, e.g., phenyltrimethylammonium hydroxide, arylalkyl, trialkyl ammonium hydroxides, e.g., benzyltrimethyl ammonium hydroxide, alkyl substituted diammonium hydroxides, e.g., bis-dibutylethylhexamethylene diammonium hydroxide, and other combinations of phase transfer catalysts and suitable bases such as suitable bases in conjunction with aryl ammonium salts, crown ethers and the like, and amine bases such as lithium, bis(trimethysilyl) amide, and the like, including mixtures thereof. Preferred materials for use as bases are tetraalkylammonium hydroxides such as tetramethylammonium hydroxide or tetrabutylammonium hydroxide.

Preferably, the base is added to the amide to produce a mixture which is then combined with the nitrobenzene. Alternatively, the base can be added after the amide and nitrobenzene have been combined. Addition of materials can be above or below surface addition.

The amount of base employed according to the invention can be conveniently expressed in terms of the ratio of equivalents of suitable base to equivalents of amide. Broadly, the ratio of equivalents of base to equivalents of amide will be about 1:1 to about 10:1, preferably about 1:1 to about 4:1, and most preferably about 1:1 to about 2:1.

The reaction is conducted at a suitable temperature which can vary over a wide range. For example, the temperature can fall within a range of from about 5° C. to about 150° C., such as from about 15° C. to about 100° C., preferably from about 25° C. to about 90° C. A most preferred temperature for conducting the reaction of the invention is from about 60° C. to about 80° C.

Control of the amount of protic material present in the reaction is important. The amount of protic material employed according to the invention can be conveniently expressed in terms of a molar ratio based on the amount of base present at the beginning of the reaction of amide and nitrobenzene. Broadly, the molar ratio of protic material to base will be less than about 5:1, preferably less than about 4:1, more preferably less than about 3:1, and most preferably less than about 1:1. Thus, the present reaction could be conducted under anhydrous conditions. As used herein, the term "controlled amount" of protic material is an amount up to that which inhibits the reaction of amide with nitrobenzene. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, xylene, and the like, including combinations thereof.

In one embodiment for controlling the amount of protic material during the reaction of amide and nitrobenzene, a desiccant is added so as to be present during the reaction of amide and nitrobenzene. For example, when the protic material is water, the desiccant removes water present during the reaction of amide and nitrobenzene and results in higher conversion of nitrobenzene and yields of p-nitroaromatic amide. As used herein, desiccant is a compound present during the reaction of amide and nitrobenzene in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina.

In another embodiment for controlling the amount of protic material during the reaction of amide and nitrobenzene, protic material is continuously removed from the reaction mixture by distillation. If the protic material present forms an azeotrope with one of the compounds in the reaction mixture, the protic material can be removed by continuous azeotropic distillation of protic material utilizing the azeotrope. The continuous removal of protic material allows the use of lower amounts of base in the reaction of amide and nitrobenzene while achieving very high conversion of nitrobenzene and excellent yields of p-nitroaromatic amide.

The reaction can be conducted under aerobic or anaerobic conditions. Under aerobic conditions, the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at room temperature and at a pressure ranging from about 0 psig (0 kg/cm$^2$) to about 250 psig (17.6 kg/cm$^2$, such as from about 14 psig (1 kg/cm$^2$) to about 150 psig (10.5 kg/cm$^2$). Under anaerobic conditions, the reaction can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention. It is currently preferred to conduct the reaction under aerobic conditions because formation of by-product azoxybenzene can be eliminated.

The p-nitroaromatic amides and/or their salts can be reduced to p-aminoaromatic amides. The neutral compounds can be generated from the salts utilizing water and/or an acid. Alternatively, the salts can be reduced. In another embodiment of the invention, p-nitroaromatic amine can be reduced to p-aminoaromatic amine. These reductions can be carried out by any of many known reductive processes, such as using a hydride source, e.g., sodium borohydride in conjunction with palladium- or platinum-on-carbon catalysts. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander, Academic Press, N.Y., page 299 (1979), which is incorporated by reference herein. The hydrogenation can be conducted in a variety of solvents including, but not limited to, toluene, xylene, aniline, ethanol, dimethylsulfoxide, water and mixtures thereof. Preferably, the hydrogenation is conducted utilizing a platinum-on-carbon or palladium-on-carbon catalyst in a suitable solvent such as, for example, either ethanol, aniline, or dimethylsulfoxide, mixtures thereof, or mixtures which include water as the solvent and a hydrogen pressure of from 100 psig (7 kg/cm$^2$) H$_2$ to about 340 psig (23.9 kg/cm$^2$) H$_2$ at a temperature of about 80° C.

Aminolysis of p-nitroaromatic amide and p-aminoaromatic amide can be conducted by reacting p-nitroaromatic amide or p-aminoaromatic amide with ammonia to produce the corresponding p-nitroaromatic amine or p-aminoaromatic amine, respectively, and the amide starting material which can be recycled. See for example, Jencks, W. P., *J. Am. Chem. Soc.*, Vol. 92, pp. 3201-3202 (1970). The ammonia can be utilized in the aminolysis reaction as either ammonia or a mixture of ammonia and ammonium hydroxide. If ammonium hydroxide is present, the reaction will produce the acid corresponding to the amide starting material in addition to the amide starting material. Preferably, p-nitroaromatic amide or p-aminoaromatic amide is reacted with ammonia in the presence of a solvent, e.g., methanol (see examples 9 and 10).

Hydrolysis of p-nitroaromatic amide and p-aminoaromatic amide can be conducted by reacting p-nitroaromatic amide or p-aminoaromatic amide with water in the presence of a suitable basic or acidic catalyst to produce the corresponding p-nitroaromatic amine or p-aminoaromatic amine, respectively, and the acid or salt thereof corresponding to the amide starting material. Examples of suitable basic catalysts include, but are not limited to, alkali metal hydroxides, alkaline earth metal hydroxides, alkali metal alkoxides, tetraalkylammonium hydroxides, ammonium hydroxide, and the like, and mixtures thereof. Examples of suitable acidic catalysts include, but are not limited to, sulfuric acid, hydrochloric acid, nitric acid, phosphoric acid, and the like, and mixtures thereof. It is currently preferred to use a basic catalyst since selected suitable bases used in the reaction of amide and nitrobenzene may also be utilized as the basic catalyst in the hydrolysis reaction. The temperature of the hydrolysis reaction will generally be in the range of about 60° C. to about 120° C.

Reductive alkylation of p-aminoaromatic amine to produce anti-oxidants or antiozonants can be conducted by any one of several well-known methods. See, for example, U.S. Pat. No. 4,900,868. Preferably, p-aminoaromatic amine and a suitable ketone or aldehyde are reacted in the presence of hydrogen and platinum-on-carbon as catalysts. Suitable ketones include, but are not limited to, methylisobutyl ketone (MIBK), acetone, methylisoamyl ketone and 2-octanone. It should be noted that reduction of p-nitroaromatic amines and alkylation of the reduced material can be conducted in the same reaction vessel utilizing the ketone as a solvent. See, for example, U.S. Pat. No. 3,414,616, U.S. Pat. No. 4,463,191, and Bannerjee et al, *J. Chem. Soc. Chem. Comm.*, 18, pp 1275-76 (1988).

Contemplated equivalents of the reactants and reagents set forth above are reactants and reagents otherwise corresponding thereto and having the same general properties wherein one or more of the various groups, e.g., —NO$_2$ are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the process of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the process of this invention. In all preparative methods, all starting materials are known or are readily preparable from known starting materials.

EXAMPLES

Materials and Methods.

Amides and nitrobenzene were reagent grade and were used without further purification. Solvents were purchased from Aldrich Chemical and were anhydrous grade. The tetramethylammonium hydroxide was purchased as the pentahydrate and used as is or was dried in a desiccator over P$_2$O$_5$ under vacuum for several days before use. Titration of the resulting solid showed the dried material to be the dihydrate. Unless indicated otherwise, all yields were determined by HPLC according to the following method. HPLC Analysis Method:

A Waters 600 series HPLC equipped with a Vydac 201HS54 (4.6×250 mm) column and UV detection at 254 nm was used to monitor all reactions. The external standard method was utilized in all the analyses. Authentic samples of products to be used as standards were prepared by known literature methods.

| Time (Min.) | Elution Gradient | |
|---|---|---|
| | % Solvent A (Water) | % Solvent B (40% Methanol in ACN) |
| 0 | 75 | 25 |
| 35 | 20 | 80 |
| 40 | 0 | 100 |
| 45 | 0 | 100 |
| 46 | 75 | 25 |
| 55 | 75 | 25 |

EXAMPLE 1

This example illustrates the direct coupling of benzamide and nitrobenzene to give 4'-nitrobenzanilide.

A solution of tetramethylammonium hydroxide dihydrate (TMA(H)·2H$_2$O) (1.8 g, 14.0 mmole), benzamide (1.2 g., 9.9 mmole) and 10 ml of xylene was stirred under nitrogen at 70° C. The water and xylene was removed by vacuum distillation at 740 mmHg/70° C. Nitrobenzene (1.2 g., 9.7 mmole) was added dropwise and the solution was stirred for 4 hours under nitrogen after which time an aliquot was removed for HPLC analysis. 4'-Nitrobenzanilide, i.e., N-(4-nitrophenyl)benzamide, was produced in 98% yield based on benzamide. Azoxybenzene was also detected as a minor product in this reaction.

EXAMPLE 2

This example illustrates the direct coupling of benzamide and nitrobenzene using DMSO as a co-solvent in the reaction.

A 100 mL round bottom flask equipped with an addition funnel and Dean-Stark trap was charged with benzamide (1.27 g., 10.4 mmole), TMA(H)·5H$_2$O (2.17 g, 11.9 mmole) and xylene (8.5 g). The xylene and water were removed by vacuum distillation (20 tort). The reaction mixture was maintained between 70°–80° C. A mixture on nitrobenzene (1.23 g, 10.0 mmole) and DMSO (1.28 g) was added dropwise to the reaction under nitrogen over 30 minutes. The reaction was maintained at 80° C. and the mixture was allowed to stir. After 4 hours an aliquot was removed and analyzed by HPLC. Yield based benzamide: 4'-nitrobenzanilide, i.e., N-(4-nitrophenyl)benzamide, 77%, azoxybenzene 9%.

EXAMPLE 3

This example illustrates the effect of protic material on the production of 4'-nitrobenzanilide, i.e., N-(4-nitrophenyl)benzamide.

A 100 mL round bottom flask equipped with an addition funnel and Dean-Stark trap was charged with benzamide (1.27 g., 10.4 mmole), TMA(H)·5H$_2$O (2.17 g, 11.9 mmole) and xylene (8.5 g). The xylene and water were removed as the azeotrope by vacuum distillation (20 tort). The reaction mixture was maintained between 70°–80° C. Various amounts of water was then added back to the reaction. Following the re-addition of water, a mixture of nitrobenzene (1.23 g, 10.0 mmole) and DMSO (1.28 g) was added dropwise to the reaction under nitrogen over 30 minutes. The reaction was maintained at 80° C. and the mixture was allowed to stir. After 4 hours an aliquot was removed and analyzed by HPLC.

TABLE 1

| Mole Ratio Water: TMA(H) | % Yield 4-Nitrobenzanilide |
|---|---|
| 10 | 0 |
| 7 | 0 |
| 3 | 5 |
| <1 | 77 |

EXAMPLE 4

This example illustrates the coupling of substituted benzamides with nitrobenzene to produce the corresponding 4'-nitrobenzanilide, i.e., N-(4-nitrophenyl)benzamide, derivatives.

To a solution containing nitrobenzene (5 g, 40.6 mmole), substituted benzamide (10.0 mmole) and 2 ml of DMSO at 70° C., TMA(H)·2H$_2$O (1.2 g, 10 mmole), was added in one portion. The reaction was allowed to stir for 4 hours after which time a sample was removed for HPLC analysis.

TABLE 2

| Substituted Benzamide | % Yield | | |
|---|---|---|---|
| | Substituted 4'-Nitrobenzanilide | Azoxybenzene | Azobenzene |
| 4-Methylbenzamide | 25 | 0.2 | 0 |
| 4-Methoxybenzamide | 16 | 0.5 | 0 |
| 4-Chlorobenzamide | 50 | 0.6 | 1.0 |
| 2-Methylbenzamide | 36 | 0.8 | 0 |
| 4-Nitrobenzamide | 6 | 0 | 0 |

EXAMPLE 5

This example illustrates the use of a variety of different bases in the reactive coupling of benzamide with nitrobenzene.

A. Tetrabutylammonium Hydroxide

Benzamide (1.2 g, 10 mmole), 40% tetrabutylammonium hydroxide in water (6.5 mL) and 1.5 mL of DMSO were charged into a three necked round bottom flask. Water was removed (5 mL) under vacuum distillation at 740 mmHG/70° C. Nitrobenzene (1.2 g, 10 mmole) was added dropwise to the reaction and the mixture was stirred under nitrogen for 4 hours. An aliquot was taken and analyzed by HPLC. Yield based on benzamide: 35% 4'-nitrobenzanilide, i.e., N-(4-nitrophenyl)benzamide, and 2.5% azoxybenzene.

B. Potassium t-Butoxide

To a solution containing 5 ml of nitrobenzene and 1.2 g of benzamide at 70° C. under nitrogen, 10 ml of (1M in THF) of potassium t-butoxide was added. The solution was stirred for 1 hour. An aliquot was taken out for HPLC analysis. No product was detected. To this reaction 18-crown-6 ether (2.6 g) was added and the reaction was stirred at 70° C. under nitrogen for 12 hours. An aliquot was taken out for HPLC analysis. Yield based on benzamide: 94% 4'-nitrobenzanilide, i.e., N-(4-nitrophenyl)benzamide, and 36% of azoxybenzene.

A similar experiment was carried out with tetrabutylammonium chloride as phase transfer catalyst. Yield based on benzamide: 29% 4'-nitrobenzanilide, i.e., N-(4-nitrophenyl)benzamide, and 10% azoxybenzene.

C. Tetrabutylammonium Chloride and Potassium Hydroxide

Tetrabutylammonium chloride (2.8 g), potassium hydroxide (1.1 g) and benzamide (1.2 g) were charged into a three necked round bottom flask. Water (10 mL) was added to the mixture and the solution was heated to 70° C. The water was removed by vacuum distillation at 740 mmHG/70° C. Nitrobenzene (1.2 g) 10 mmole) was added dropwise and the solution was stirred for 4 hours with continuous removal of water. An aliquot was taken out for HPLC analysis. Yield based on benzamide: 57% 4'-nitrobenzanilide, i.e., N-(4-nitrophenyl)-benzamide, and 1.5% of azoxybenzene.

A similar experiment was carried out using 18-crown-6 ether as a phase transfer catalyst. Yield based on benzamide: 26% 4'-nitrobenzanilide, i.e., N-(4-nitrophenyl)benzamide, and 2.5% azoxybenzene.

D. Isopropylmagnesium Chloride

A solution of isopropylmagnesium chloride (2M in THF) was added to a suspension of 1.2 g of benzamide in 5 ml of xylene in an ice bath under nitrogen. After addition was completed, all of the solvents were removed at 740 mmHG/80° C. until dried. DMSO (5 mL) was added followed by the dropwise addition of nitrobenzene (1.2 g, 10 mole). The solution was stirred at 80° C. for 4 hours under nitrogen. An aliquot was taken for HPLC analysis. Yield based on benzamide: 32% 4'-nitrobenzanilide, i.e., N-(4-nitrophenyl)benzamide, and 1.3% of azoxybenzene.

EXAMPLE 6

This example illustrates the coupling of benzamide and nitrobenzene in various solvent systems.

In a typical experiment, 1.2 g of nitrobenzene, 1.8 g TMA(H)·2H$_2$O, 1.2 g of benzamide and 10 ml solvent was stirred under nitrogen at 70° C. for 12 hours. An aliquot was removed for HPLC analysis. Yields were based on benzamide.

TABLE 3

| Solvent | % Yield | | |
|---|---|---|---|
| | 4'-Nitro-benzanilide | Azoxybenzene | Azobenzene |
| Pyridine | 19 | 6.5 | 0 |
| Xylene | 0 | 0 | 0 |
| N-Methyl-aniline | 6.3 | 9.5 | 0 |
| Chlorobenzene | 69 | 2 | 0 |
| NMP | 39 | 1.5 | 4.8 |
| Nitrobenzene | 100 | 48 | — |

EXAMPLE 7

This example illustrates the hydrogenation of 4'-nitrobenzanilide, i.e., N-(4-nitrophenyl)benzamide, to 4'-aminobenzanilide, i.e., N-(4-aminophenyl)benzamide using various solvents.

All reactions were carried out in a 300 mL stainless steel autoclave. Thus, 4-nitrobenzanilide (1.0 g, 4.13 mmole) and 3% Pt/carbon catalyst (0.033 g dry weight) was charged into the clave with 80 mL of solvent. The vessel was purge with nitrogen and then was pressurized with 200 psig (14.1 kg/cm$^2$) hydrogen. The solution was heated to 80° C. and agitated at 1500 rpm. Hydrogen uptake was immediately observed. The reaction was considered complete when hydrogen uptake ceased. The mixture was cooled, filtered and a sample was analyzed by HPLC.

TABLE 4

| Solvent | Dry Weight Catayst (g) | Conversion | Yield |
|---|---|---|---|
| Ethanol | 0.033 | 100% | 100% |
| DMSO | 0.033 | 94% | 52% |
| Aniline | 0.033 | 100% | 100% |

EXAMPLE 8

This example illustrates the hydrogenation of the tetramethylammonium salt of 4'-nitrobenzanilide, i.e., N-(4-nitrophenyl)benzamide, to 4'-aminobenzanilide, i.e., N-(4-aminophenyl)benzamide, using various solvents.

All reactions were carried out in a 300 mL stainless steel autoclave. Thus, 4'-nitrobenzanilide (1.21 g, 5.0 mmole) and TMA(H)·2H$_2$O (7.0 mmole) was mixed in 80 mL of solvent. This mixture was charged into the clave with 3% Pt/Carbon catalyst (0.033 g dry weight). The reaction vessel was purged with nitrogen and was then charged with hydrogen at 200 psig (14.1 kg/cm$^2$). The reaction was heated to 80° C. and agitated at 1500 rpm. Hydrogen uptake was immediately observed. The reaction was considered complete when hydrogen uptake ceased. The mixture was cooled, filtered, and a sample was removed for HPLC analysis.

TABLE 5

| Solvent | Dry Weight Catayst (g) | Conversion | Yield |
|---|---|---|---|
| Ethanol | 0.033 | 100% | 100% |
| DMSO | 0.033 | 50% | 17% |
| Aniline | 0.033 | 100% | 100% |

EXAMPLE 9

This example illustrates the aminolysis of 4'-nitrobenzanilide, i.e., N-(4-nitrophenyl)benzamide, in methanol to give 4-nitroaniline.

Approximately 10 ml of liquid ammonia was added rapidly to a solution of 100 mg of 4'-nitrobenzanilide and 50 ml of methanol in a Parr bomb at −50° C. The Parr reactor was stirred at 120° C./300 psi (21.1 kg/cm$^2$) for 3 days. After the reactor was cooled to −50° C., the pressure was released and the reactor was opened. An aliquot was taken out for HPLC analysis which revealed a 50% yield of 4-nitroaniline and benzamide. The remainder of the material was unreacted.

EXAMPLE 10

This example illustrates the aminolysis of 4'-aminobenzanilide, i.e., N-(4-aminophenyl)benzamide, in methanol to give 1,4-phenylenediamine.

Approximately 10 ml of liquid ammonia was added rapidly to a solution of 100 mg of 4'-nitrobenzanilide and 50 ml of methanol in a Parr bomb at −50° C. The Parr reactor was stirred at 200° C./300 psi (21.1 kg/cm$^2$) for 3 days. After the reactor was cooled to −50° C., the pressure was released and the reactor was opened. An aliquot was taken out for HPLC analysis and compared with authentic samples. HPLC analysis showed 40% yield of 1,4-phenylenediamine and benzamide. The remainder of the material was unreacted.

EXAMPLE 11

This example illustrates the reaction of an aliphatic amide with nitrobenzene.

A solution of 0.2 g of isobutyramide and 5 ml of nitrobenzene was heated to 80° C. under nitrogen. Tetramethylammonium hydroxide dihydrate (1.8 g) was added all at once. The solution was stirred for 1 hour. An aliquot was taken out for HPLC analysis. Yield based on isobutyramide: 19% p-(N-nitrophenyl)butyramide.

EXAMPLE 12

This example illustrates the elimination of azoxybenzene as a by-product of the reaction of aromatic amides with nitrobenzene under aerobic conditions with continual removal of water.

A 100 mL three-necked round-bottom flask was charged with 10 mmole of benzamide, 10 mmole of tetramethylammonium hydroxide dihydrate and 10 g of nitrobenzene. The solution was heated to 75°-80° C. with air blowing subsurface into the solution via a syringe. This constant stream of air removed water and nitrobenzene continually from the reaction and it was collected in a dry ice acetone trap. 10 ml of methanol/acetonitrile (4:6) solution was added at the end of the reaction time to homogenize the solution. A weighted aliquot was sampled for HPLC assay and the yield of N-(4-nitrophenyl)benzamide is given in Table 6.

Three additional runs were made replacing benzamide with the aromatic amides listed in Table 6 and the yield of the corresponding N-(4-nitrophenyl) substituted benzamide reported.

TABLE 6

| Amide | Reaction Time (hrs) | Yield |
| --- | --- | --- |
| Benzamide | 2 | 80% |
| 4-Methoxybenzamide | 18 | 61% |
| 4-Nitrobenzamide | 18 | 41% |
| 4-Toluamide | 18 | 63% |

EXAMPLE 13

This example illustrates the elimination of azoxybenzene as a by-product in the reaction of aromatic amides with nitrobenzene under aerobic conditions without the continual removal of water.

Benzamide (10 mmole) and 10 mmole of tetramethylammonium hydroxide in 10 g of nitrobenzene was stirred at 75°-80° C./56-63 psi (3.9 −4.4 kg/cm$^2$) oxygen for 12 hours. Methanol/acetonitrile (4:6) (10 mL) solution was then added to homogenize the solution. A weighted aliquot was sampled for HPLC assay and revealed 20% yield of 4-nitrobenzanilide, i.e., N-(4-nitrophenyl)benzamide. No azoxybenzene was detected.

EXAMPLE 14

This example illustrates the improved yields obtained in the reaction of benzamide and nitrobenzene under aerobic conditions.

A three-necked round-bottom flask equipped with a Dean-Strak trap and gas inlet line was charged with benzamide (0.2 mole), tetramethylammonium hydroxide dihydrate (0.2 mole) and nitrobenzene (100 mL). The reaction was stirred for 8 hours at 65° C. with a continuous stream of air sweeping the surface of the reaction. Approximately 5 mL of water and 40 mL of nitrobenzene was collected in the Dean-Stark trap. Another 100 mL of nitrobenzene was added and the reaction was allowed to stir overnight. A total of 70 mL of nitrobenzene was collected over this time period. The solution was cooled and water was added which caused the immediate precipitation of 4-nitrobenzanilide, i.e., N-(4-nitrophenyl)benzamide. The solution was filtered and a dark brown solid was obtained. The solid was washed with hot hexane and air dried to obtain 43.5 g of 4-nitrobenzanilide (90% yield).

EXAMPLE 15

This example illustrates the generation of 4-nitroaniline by hydrolysis of the tetramethylammonium salt of N-(4-nitrophenyl)benzamide.

A solution of 10 mmole of benzamide, 10 mmole tetramethylammonium hydroxide dihydrate in 10 g of nitrobenzene was stirred under vacuum (40 mmHg absolute) at 65° C. for 1 hour. During this time nitrobenzene and water were being continuously distilled from the reaction. Analysis of the reaction mixture by reverse phase HPLC revealed N-(4-nitrophenyl)benzamide was produced in 99% yield. Water (50 mL) was added to the reaction mixture and the solution was stirred for an additional hour at 70° C. The organic layer of the two phase mixture was separated and analyzed by reverse-phase HPLC. 4-Nitroaniline was generated in 90% yield based on benzamide charged.

What is claimed is:

1. A process for preparing N-(4-nitroaromatic) amides comprising:
   (a) contacting an amide and nitrobenzene in the presence of a suitable solvent system, and
   (b) reacting the amide and nitrobenzene in the presence of a suitable base and a controlled amount of protic material at a suitable temperature in a confined reaction zone.

2. The process of claim 1 wherein said amide is selected from the group consisting of aromatic amides, aliphatic amides, substituted aromatic amide derivatives, substituted aliphatic amide derivatives and diamides having the formula:

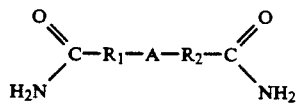

wherein $R_1$ and $R_2$ are independently selected from the group consisting of aromatic groups, aliphatic groups and a direct bond, and A is selected from the group consisting of

—SO$_2$—, —O—, —S— and a direct bond.

3. The process of claim 2 wherein said aliphatic amides and said substituted aliphatic amide derivatives are represented by the formula:

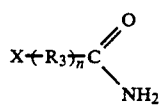

wherein n is 0 or 1, R₃ is selected from the group consisting of alkyl, aryl alkyl, alkenyl, arylalkenyl, cycloalkyl and cycloalkenyl groups and X is selected from the group consisting of hydrogen, —NO₂, NH₂, aryl groups, alkoxy groups, sulfonate groups, —SO₃H, —OH, —COH, —COOH, and alkyl, aryl, arylalkyl or alkylaryl groups containing at least one —NH₂ group.

4. The process of claim 3 wherein said aliphatic amides and said substituted aliphatic amide derivatives are selected from the group consisting of isobutyramide, urea, acetamide and propyl amide.

5. The process of claim 2 wherein the substituent of said substituted aromatic amide derivatives is selected from the group consisting of halides, —NO₂, —NH₂, alkyl groups, alkoxy groups, sulfonate groups, —SO₃H, —OH, —OH, —COOH and alkyl, aryl, arylalkyl or alkylaryl groups containing at least one —NH₂ group, wherein halides are selected from the group consisting of chloride, bromide and fluoride.

6. The process of claim 5 wherein said aromatic amides and said substituted aromatic amide derivatives are selected from the group consisting of benzamide, 4-methylbenzamide, 4-methoxybenzamide, 4-chlorobenzamide, 2-methylbenzamide, 4-nitrobenzamide, and 4-aminobenzamide.

7. The process of claim 2 wherein said diamides are selected from the group consisting of adipamide, oxalic amide, terephthalic diamide, and 4,4'-biphenyldicarboxamide.

8. The process of claim 1 wherein said suitable solvent system includes a solvent selected from the group consisting of nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxide or amides having a melting point below the reaction temperature and mixtures thereof.

9. The process of claim 8 wherein said suitable solvent system includes a protic solvent.

10. The process of claim 1 wherein the molar ratio of said protic material to said suitable base is less than about 5:1 and the ratio of equivalents of said suitable base to equivalents of said amide is about 1:1 to about 10:1.

11. The process of claim I wherein said suitable temperature is from about 5° C. to about 150° C.

12. The process of claim i wherein said suitable base is selected from the group consisting of organic and inorganic bases.

13. The process of claim 12 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

14. The process of claim 1 wherein said base is selected from the group consisting of an aryl ammonium, alkyl ammonium, aryl/alkyl ammonium and alkyl diammonium salt in conjunction with a base source.

15. The process of claim 1 wherein said solvent is nitrobenzene and said base is a tetraalkyl ammonium hydroxide.

16. The process of claim 1 wherein said solvent and said base is a tetraalkyl ammonium hydroxide and said temperature is above the melting point of said tetraalkyl ammonium hydroxide.

17. The process of claim 1 wherein said amide and nitrobenzene are reacted under aerobic conditions.

18. The process of claim 1 wherein said amide and nitrobenzene are reacted under anaerobic conditions.

19. The process of claim 1 wherein a desiccant is present during Step (b) to control the amount of protic material present during the reaction of amide and nitrobenzene.

20. The process of claim 1 wherein the amount of protic material is Step (b) is controlled by the continuous distillation of said protic material.

21. A process for preparing N-(4-aminoaromatic) amides comprising:
    (a) contacting an amide and nitrobenzene in the presence of a suitable solvent system,
    (b) reacting the amide and nitrobenzene in the presence of a suitable base and a controlled amount of protic material at a suitable temperature in a confined reaction zone, and
    (c) reducing the reaction product of (b) under conditions which produce N-(4-aminoaromatic) amides.

22. The process of claim 21 wherein said amide is selected from the group consisting of aromatic amides, aliphatic amides, substituted aromatic amide derivatives, substituted aliphatic amide derivatives and diamides having the formula:

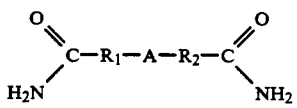

wherein R₁ and R₂ are independently selected from the group consisting of aromatic groups, aliphatic groups and a direct bond, and A is selected from the group consisting of

—SO₂—, —O—, —S— and a direct bond.

23. The process of claim 22 wherein said aliphatic amides and said substituted aliphatic amide derivatives are represented by the formula:

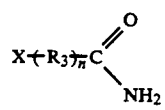

wherein n is 0 or 1, R₃ is selected from the group consisting of alkyl, arylalkyl, alkenyl, arylalkenyl, cycloalkyl and cycloalkenyl groups and X is selected from the group consisting of hydrogen, —NO₂, —NH₂, aryl groups, alkoxy groups, sulfonate groups, —SO₃H, —OH, —COH, —COOH, and alkyl, aryl, arylalkyl or alkylaryl groups containing at least one —NH₂ group.

24. The process of claim 23 wherein said aliphatic amides and said substituted aliphatic amide derivatives are selected from the group consisting of isobutyramide, urea, acetamide and propyl amide.

25. The process of claim 22 wherein the substituent of said substituted aromatic amide derivatives is selected from the group consisting of halides, —NO$_2$, —NH$_2$, alkyl groups, alkoxy groups, sulfonate groups, —SO$_3$H, —OH, —COH, —COOH and alkyl, aryl, arylalkyl or alkyl aryl groups containing at least one —NH$_2$ group, wherein halides are selected from the group consisting of chloride, bromide and fluoride.

26. The process of claim 25 wherein said aromatic amides and said substituted aromatic amide derivatives are selected from the group consisting of benzamide, 4-methylbenzamide, 4-methoxybenzamide, 4-chlorobenzamide, 2-methylbenzamide, 4-nitrobenzamide, and 4-aminobenzamide.

27. The process of claim 22 wherein said diamides are selected from the group consisting of adipamide, oxalic amide, terephthalic diamide, and 4,4'-biphenyldicarboxamide.

28. The process of claim 21 wherein said suitable solvent system includes a solvent selected from the group consisting of nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxide or amides having a melting point below the reaction temperature and mixtures thereof.

29. The process of claim 28 wherein said suitable solvent system includes a protic solvent.

30. The process of claim 21 wherein the molar ratio of said protic material to said suitable base is less than about 5:1 and the ratio of equivalents of said suitable base to equivalents of said amide is about 1:1 to about 10:1.

31. The process of claim 21 wherein said suitable temperature is from about 5° C. to about 150° C.

32. The process of claim 21 wherein said suitable base is selected from the group consisting of organic and inorganic bases.

33. The process of claim 32 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

34. The process of claim 21 wherein said base is selected from the group consisting of an aryl ammonium, alkyl ammonium, aryl/alkyl ammonium and alkyl diammonium salt in conjunction with a base source.

35. The process of claim 21 wherein said solvent is nitrobenzene and said base is a tetraalkyl ammonium hydroxide.

36. The process of claim 21 wherein said solvent and said base is a tetraalkyl ammonium hydroxide and said temperature is above the melting point of said tetraalkyl ammonium hydroxide.

37. The process of claim 21 wherein said amide and nitrobenzene are reacted under aerobic conditions.

38. The process of claim 21 wherein said amide and nitrobenzene are reacted under anaerobic conditions.

39. The process of claim 21 wherein a desiccant is present during Step (b) to control the amount of protic material present during the reaction of amide and nitrobenzene.

40. The process of claim 21 wherein the amount of protic material is Step (b) is controlled by the continuous distillation of said protic material.

41. The process of claim 21 further comprising:
(d) reacting the N-(4-aminoaromatic) amide with ammonia under conditions which produce the corresponding N-(4-aminoaromatic) amine and amide.

42. The process of claim 41 further comprising:
(e) reductively alkylating the N-(4-aminoaromatic) amine to produce alkylated N-(4-aminoaromatic) amine.

43. The process of claim 42 wherein said N-(4-aminoaromatic) amine is reductively alkylated utilizing a compound selected from the group consisting of ketones and aldehydes.

44. The process of claim 43 wherein said ketone is selected from the group consisting of acetone, methylisobutylketone, methylisoamylketone and 2-octanone.

45. The process of claim 21 further comprising:
(d) reacting the N-(4-aminoaromatic) amide with water in the presence of a suitable basic or acidic catalyst under conditions which produce the corresponding N-(4-aminoaromatic) amine and the acid or salt thereof corresponding to said amide of (a).

46. The process of claim 45 further comprising:
(e) reductively alkylating the N-(4-aminoaromatic) amine to produce alkylated N-(4-aminoaromatic) amine.

47. The process of claim 46 wherein said N-(4-aminoaromatic) amine is reductively alkylated utilizing a compound selected from the group consisting of ketones and aldehydes.

48. The process of claim 47 wherein said ketone is selected from the group consisting of acetone, methylisobutylketone, methylisoamylketone and 2-octanone.

49. A process for preparing N-(4-nitroaromatic) amine comprising:
(a) contacting an amide and nitrobenzene in the presence of a suitable solvent system,
(b) reacting the amide and nitrobenzene in the presence of a suitable base and a controlled amount of protic material at a suitable temperature in a confined reaction zone, and
(c) reacting the reaction product of (b) with (i) ammonia or (ii) water in the presence of a suitable basic or acidic catalyst under conditions which produce the corresponding N-(4-nitroaromatic) amine and amide or the corresponding acid or salt thereof.

50. The process of claim 49 wherein said amide is selected from the group consisting of aromatic amides, aliphatic amides, substituted aromatic amide derivatives, substituted aliphatic amide derivatives and diamides having the formula:

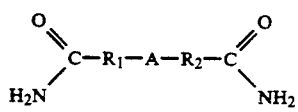

wherein R$_1$ and R$_2$ are independently selected from the group consisting of aromatic groups, aliphatic groups and a direct bond, and A is selected from the group consisting of

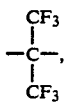

—SO₂—, —O—, —S— and a direct bond.

51. The process of claim 50 wherein said aliphatic amides and said substituted aliphatic amide derivatives are represented by the formula:

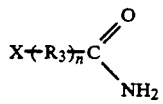

wherein n is 0 or 1, R₃ is selected from the group consisting of alkyl, arylalkyl, alkenyl, arylalkenyl, cycloalkyl and cycloalkenyl groups and X is selected from the group consisting of hydrogen, —NO₂, —NH₂, aryl groups, alkoxy groups, sulfonate groups, —SO₃H, —OH, —COH, —COOH, and alkyl, aryl, arylalkyl or alkylaryl groups containing at least one —NH₂ group.

52. The process of claim 51 wherein said aliphatic amides and said substituted aliphatic amide derivatives are selected from the group consisting of isobutyramide, urea, acetamide and propylamide.

53. The process of claim 50 wherein the substituent of said substituted aromatic amide derivatives is selected from the group consisting of halides, —NO₂, —NH₂, alkyl groups, alkoxy groups, sulfonate groups, —SO₃H, —OH, —COH, —COOH and alkyl, aryl, arylalkyl or alkylaryl groups containing at least one —NH₂ group, wherein halides are selected from the group consisting of chloride, bromide and fluoride.

54. The process of claim 53 wherein said aromatic amides and said substituted aromatic amide derivatives are selected from the group consisting of benzamide, 4-methylbenzamide, 4-methoxybenzamide, 4-chlorobenzamide, 2-methylbenzamide, 4-nitrobenzamide, and 4-aminobenzamide.

55. The process of claim 50 wherein said diamides are selected from the group consisting of adipamide, oxalic amide, terephthalic diamide, and 4,4′-biphenyldicarboxamide.

56. The process of claim 49 wherein said suitable solvent system includes a solvent selected from the group consisting of nitrobenzene, dimethylsulfoxide, dimethylformamide, N-methyl-2-pyrrolidone, pyridine, N-methylaniline, chlorobenzene, tetrahydrofuran, 1,4-dioxane, tetraalkyl ammonium hydroxide or amides having a melting point below the reaction temperature and mixtures thereof.

57. The process of claim 56 wherein said suitable solvent system includes a protic solvent.

58. The process of claim 49 wherein the molar ratio of said protic material to said suitable base is less than about 5:1 and the ratio of equivalents of said suitable base to equivalents of said amide is about 1:1 to about 10:1.

59. The process of claim 49 wherein said suitable temperature is from about 5° C. to about 150° C.

60. The process of claim 49 wherein said suitable base is selected from the group consisting of organic and inorganic bases.

61. The process of claim 60 wherein said organic and inorganic bases are selected from the group consisting of alkali metals, alkali metal hydrides, alkali metal hydroxides, alkali metal alkoxides, phase transfer catalyst in conjunction with a base source, amines, crown ethers in conjunction with a base source, alkyl magnesium halides, and mixtures thereof.

62. The process of claim 49 wherein said base is selected from the group consisting of an aryl ammonium, alkyl ammonium, aryl/alkyl ammonium and alkyl diammonium salt in conjunction with a base source.

63. The process of claim 49 wherein said solvent is nitrobenzene and said base is a tetraalkyl ammonium hydroxide.

64. The process of claim 49 wherein said solvent and said base is a tetraalkyl ammonium hydroxide and said temperature is above the melting point of said tetraalkyl ammonium hydroxide.

65. The process of claim 49 wherein said amide and nitrobenzene are reacted under aerobic conditions.

66. The process of claim 49 wherein said amide and nitrobenzene are reacted under anaerobic conditions.

67. The process of claim 49 wherein a desiccant is present during Step (b) to control the amount of protic material present during the reaction of amide and nitrobenzene.

68. The process of claim 49 wherein the amount of protic material is Step (b) is controlled by the continuous distillation of said protic material.

69. The process of claim 49 further comprising:
(d) reducing the N-(4nitroaromatic) amine under conditions which produce the corresponding N-(4-aminoaromatic) amine.

70. The process of claim 69 further comprising:
(e) reductively alkylating the N-(4-aminoaromatic) amine to produce alkylated N-(4-aminoaromatic) amine.

71. The process of claim 70 wherein said N-(4-aminoaromatic) amine is reductively alkylated utilizing a compound selected from the group consisting of ketones and aldehydes.

72. The process of claim 71 wherein said ketone is selected from the group consisting of acetone, methylisobutylketone, methylisoamylketone and 2-octanone.

73. The process of claim 49 further comprising:
(d) reductively alkylating the N-(4-nitroaromatic) amine to produce alkylated N-(4-aminoaromatic) amine.

74. The process of claim 73 wherein said N-(4nitroaromatic) amine is reductively alkylated utilizing a compound selected from the group consisting of ketones and aldehydes.

75. The process of claim 74 wherein said ketone is selected from the group consisting of acetone, methylisobutylketone, methylisoamylketone and 2-octanone.

76. The process of claim 49 comprising:
(a) contacting an amide and nitrobenzene in the presence of a suitable solvent system;
(b) reacting the amide and nitrobenzene in the presence of a suitable base and a controlled amount of protic material at a suitable temperature in a confined reaction zone, and
(c) reacting the reaction product of (b) with ammonia under conditions which produce the corresponding N-(4nitroaromatic) amine and amide.

77. The process of claim 49 comprising:
(a) contacting an amide and nitrobenzene in the presence of a suitable solvent system;
(b) reacting the amide and nitrobenzene in the presence of a suitable base and a controlled amount of protic material at a suitable temperature in a confined reaction zone, and (c) reacting the reaction product of (b) with water in the presence of a suitable basic or acidic catalyst under conditions which produce the corresponding N-(4-nitroaromatic) amine and the acid or salt thereof corresponding to said amide of (a).

* * * * *